United States Patent [19]

Bowsher et al.

[11] Patent Number: 4,582,806
[45] Date of Patent: Apr. 15, 1986

[54] PURIFICATION OF PHENYLETHANOLAMINE N-METHYLTRANSFERASE

[75] Inventors: Ronald R. Bowsher, Beech Grove; David P. Henry, Indianapolis, both of Ind.

[73] Assignee: Eli Lilly and Company, Indianapolis, Ind.

[21] Appl. No.: 627,320

[22] Filed: Jul. 2, 1984

[51] Int. Cl.$^4$ .......................... C12N 9/10; C12Q 1/48
[52] U.S. Cl. ...................................... 435/193; 435/15; 435/814; 435/815; 435/816
[58] Field of Search .................................. 435/193, 15

[56] References Cited

U.S. PATENT DOCUMENTS 4,288,542  9/1981  Johnson et al. ...................... 435/15
4,311,790  1/1982  Vlachakis ............................. 435/15

OTHER PUBLICATIONS

Journal of Biochemical and Biophysical Methods, vol. 4 (1981) 255-259.
Axelrod in Methods in Enzymology, vol. 17, part B, pp. 761-764 (1971).
Henry et al., "A Sensitive . . . Plasma," *Life Sciences*, vol. 16, 375-384 (1975).
Falke et al., "Radioenzymatic . . . Extraction," *Clinica Chimica Acta*, 89, 111-117 (1978).
Axelrod, "Purification . . . Transferase," *The Journal of Biological Chemistry*, vol. 237, No. 5, 1657-1660 (1962).
Molinoff et al., "A Sensitive . . . Dopamine-$\beta$-Hydroxylase," *The Journal of Pharmacology and Experimental Therapeutics*, vol. 178, No. 3, 425-431 (1971).
Fuller et al., "A Micromethod . . . Transferase," *Analytical Biochemistry*, 16, 349-354 (1966).
Connett et al., "Purification . . . N-methyltransferase", *The Journal of Biological Chemistry*, vol. 245, No. 2, 329-334 (1970).
Joh et al., "Isolation . . . N-methyltransferase", *Molecular Pharmacology*, 9, 117-129 (1973).

Primary Examiner—Lionel M. Shapiro
Attorney, Agent, or Firm—Bruce J. Barclay; Arthur R. Whale

[57] ABSTRACT

The present invention provides an efficient process for purifying the enzyme phenylethanolamine N-methyltransferase suitable for use in radioenzymatic assays of endogenous compounds.

5 Claims, No Drawings

PURIFICATION OF PHENYLETHANOLAMINE N-METHYLTRANSFERASE

BACKGROUND OF THE INVENTION

The mammalian sympathetic nervous system is composed of various cellular tissues having the unique capability of synthesizing postsynaptic neurotransmitter compounds. These compounds are biogenic amines termed catecholamines, a term derived from the catechol, or dihydroxybenzene, nucleus common to each of the compounds. These catecholamines include dopamine, norepinephrine and epinephrine.

Aberrations of the sympathetic nervous system can lead to a wide variety of adverse clinical manifestations. Therefore, accurate and reliable methods for quantifying the concentration of catecholamines in the body are critical to provide adequate monitoring of the system. Further, since these compounds are present in the body in very small amounts, the methods must be highly sensitive, that is, capable of detecting the compounds in very small amounts. The frequency at which these methods are conducted mandate further that they be highly reproducible under laboratory conditions when employing a variety of body tissues and fluids and provide the results quickly in order to facilitate diagnosis.

Radioenzymatic assays are sensitive analytical methods which have found wide use in the quantification of various biogenic amines. These assays are based on the enzymatic methylation of a specified compound to a radiolabeled product by an appropriate enzyme employing radioactive S-adenosylmethionine as the methyl donor. Most of the currently employed radioenzymatic assays lack the sensitivity necessary to quantify catecholamines in important biological samples, such as human plasma.

Henry et al. in *Life Sciences* 16:375 (1975) describe a useful radioenzymatic assay for specifically measuring norepinephrine in tissues, plasma and urine. This method relates to the conversion of norepinephrine to radiolabeled epinephrine employing partially purified bovine adrenal phenylethanolamine N-methyltransferase and tritiated S-adenosylmethionine.

Since the first disclosure of the phenylethanolamine N-methyltransferase based norepinephrine radioenzymatic assay described above, research has continued in an effort to improve the assay in order to provide maximal sensitivity and specificity. It has been determined that the enzymatic conversion of norepinephrine to epinephrine is severely inhibited by endogenous substances contained in partially purified phenylethanolamine N-methyltransferase enzyme preparations.

Known procedures for partially purifying phenylethanolamine N-methyltransferase exist but are incapable of removing contaminating methyltransferase enzymes and other substances. Competing methyltransferases of particular importance due to their high activity and widespread distribution in mammalian tissues include the protein methyltransferases and sulfhydryl methyltransferase. Further, sulfhydryl reducing agents such as dithiothreitol have been employed in radioenzymatic assays as antioxidants for catecholamines. Many of these compounds are substrates for sulfhydryl methyltransferases.

The use of phenylethanolamine N-methyltransferase contaminated with other methyltransferases reduces the sensitivity of the assay by reducing the rate of conversion of substrate to product and by increasing assay blanks. The amount of radiolabeled epinephrine produced is reduced since the contaminant methyltransferases exhaust the methyl donor S-adenosylmethionine and generate S-adenosylhomocysteine, a known potent methyltransferase inhibitor.

Several major problems exist in isolating phenylethanolamine N-methyltransferase in sufficient purity to be suitable for use in radioenzymatic assays. The first problem is that the enzyme exists in multiple charge and molecular weight forms. Secondly, various catecholamines copurify with other large molecular weight substances such as phenylethanolamine N-methyltransferase.

The present invention overcomes these problems and provides a process for purifying phenylethanolamine N-methyltransferase in high yield suitable for use in the analysis of a number of biogenic amines. More specifically, this process can be conducted under standard laboratory conditions within a comparatively short time to provide purified phenylethanolamine N-methyltransferase capable of providing maximal conversion of norepinephrine to tritiated epinephrine.

SUMMARY OF THE INVENTION

The present invention relates to a method for isolating phenylethanolamine N-methyltransferase in substantially pure form from enzyme containing mammalian tissues at a temperature in the range of about 0° C. to about 5° comprising the following steps:

A. disrupting the mammalian tissue in the presence of an isotonic media and isolating the phenylethanolamine N-methyltransferase;
B. fractionating the supernatant in (A) with ammonium sulfate at about 55% to about 85% saturation and collecting the precipitate.
C. suspending the precipitate formed in (B) with a suitable buffer having a pH in the range of about 7.0 to 9.0;
D. adjusting the pH of the suspension in (C) to about 4.5 to 5.5 with an appropriate weak acid;
E. dialyzing the suspension in (D) against a sodium acetate buffer having a pH in the range of about 4.5 to 5.5;
F. concentrating the enzyme preparation in (E) by ammonium sulfate fractionation at about 55% to about 85% saturation and desalting;
G. purifying the enzyme preparation in (F) with anion-exchange chromatography;
H. purifying the enzyme preparation in (G) with molecular size exclusion chromatography; and
I. purifying the enzyme preparation in (H) with boronate-agarose chromatography.

DETAILED DESCRIPTION OF THE INVENTION

The accepted biosynthetic pathway for neurotransmitters in the sympathetic nervous system was first postulated by Blaschko in 1939. This pathway suggested the conversion of norepinephrine to epinephrine by the enzyme phenylethanolamine N-methyltransferase. In mammals, it has been determined that this enzyme is localized almost exclusively in the adrenal gland with trace amounts also present in the heart and brain. Thus, while the adrenal medulla represents the preferred tissue source for the isolation of phenylethanolamine N-methyltransferase, due to size limitations of adrenals of most species the only practical source of the enzyme is bovine glands.

Once isolated, the enzyme containing mammalian tissue is immediately chilled, for example by submersion in an isotonic solution of sodium chloride. When used, the temperature of this solution is maintained in the range of about 0° C. to about 5° C. This temperature range is also employed for all subsequent steps of the present purification method as well. Typically, once in the laboratory, any fat or cortical tissue is removed from around the mammalian tissue to provide only enzyme containing mammalian tissue. When using adrenal glands, the adrenal cortex is also removed due to its high lipid content which hinders subsequent enzyme purification.

The mammalian tissue thus isolated must be disrupted in order to facilitate extraction of the enzyme. Tissue disruption may be conducted mechanically by any of several well known procedures such as sonication, by means of a tissue press or preferably by homogenization. Homogenization may be conducted by any one of several routine procedures but is preferably carried out by first mincing the enzyme containing tissue into small pieces and then combining these pieces with an isotonic media in an homogenizer. Homogenizers suitable for use herein include blenders and other instruments, such as a Brinkmann Polytron. Suitable isotonic media include potassium chloride or phosphate buffer. The preferred isotonic media is an isotonic sucrose solution. While the amount of isotonic media employed should be sufficient to completely solubilize the enzyme, the isotonic media is preferably employed at a volume of approximately 3 to 10 times the volume of the mammalian tissue sample.

The tissue suspension is then centrifuged for a period of about 15 to 60 minutes at a force in the range of about $10000 \times g$ to about $60000 \times g$. Centrifugation is preferably conducted for about 15 minutes at a force of about $40000 \times g$. The supernatant thus formed is then filtered, typically through gauze, so as to remove the lipid layer. The filtered supernatant is then typically centrifuged at a force of about $100,000 \times g$ to $300,000 \times g$ for a period of about 15 to about 120 minutes so as to remove storage granules known to contain high levels of norepinephrine and epinephrine. Centrifugation is preferably conducted at a force of about $220,000 \times g$ for a period of approximately 90 minutes.

The supernatant thus prepared is isolated and slurried with solid enzyme-grade ammonium sulfate which causes the enzyme to precipitate. The purpose of the ammonium sulfate precipitation is to remove any soluble norepinephrine or epinephrine and to simultaneously concentrate the enzyme preparation. The ammonium sulfate is employed at a concentration in the range of about 55% to about 85%, more preferably at a concentration to provide about a 65% saturated solution of ammonium sulfate (413 g of ammonium sulfate for each 1000 ml of enzyme preparation). The preparation is stirred for a period of about 5 to about 60 minutes, preferably for about 20 minutes, and centrifuged at about $40000 \times g$ for about 10 minutes.

The supernatant is discarded and the precipitate is suspended with a suitable buffer having a pH in the range of about 7.0 to 9.0. Suitable buffers for use in the present purification method will have a pH in the range of about 7.0 to about 9.0 and should be cation buffers such as tris, bis-tris and bis-tris propane. These buffers are known in the biochemical art and commercially available. The preferred buffer employed in the suspension of the precipitate is a solution of tris(hydroxymethyl)aminomethane and a chelating agent such as ethylenediaminetetraacetic acid (EDTA).

The pH of the enzyme preparation is adjusted to approximately 4.5 to 5.5 by the slow addition of an appropriate weak acid, which is any acid capable of forming a buffer in this pH range. The preferred weak acid employed herein is cold acetic acid. This mixture is then centrifuged and the supernatant is decanted and transferred to dialysis bags.

The supernatant is dialyzed for approximately 24 hours against a sodium acetate solution at pH of approximately 4.5 to 5.5. Typically one buffer change is required although more may be employed as needed. It should also be noted that during the dialysis process additional protein will typically precipitate. The dialyzed preparation is then centrifuged and the supernatant is decanted. The precipitate is discarded. The supernatant is titrated to a pH of approximately 7.0 to 7.5 upon the slow addition of a base such as ammonium hydroxide and adjusted to a concentration of approximately 1 mM by the addition of dipotassium EDTA.

The dialysis procedure described above has two functions. First, dialysis at an acidic pH efficiently removes endogenous norepinephrine and epinephrine. Secondly, substantial enzyme purification is achieved since phenylethanolamine N-methyltransferase is very stable at a pH around 5, while approximately two-thirds of the other total proteins are removed at this step. Further, it is believed that pH 5 treatment is an efficient process for removing endogenous thiol S-methyltransferase, a known inhibitor of enzyme activity.

The enzyme preparation described above is concentrated by precipitation with ammonium sulfate fractionation at about 55% to about 85% saturation. This preparation is typically about 65% saturated. The precipitate is collected and centrifuged and the supernatant is suspended in a suitable buffer-EDTA system as described above at a pH of approximately 8.

The enzyme buffer solution is next desalted by dialysis or by molecular exclusion chromatography which is capable of separating molecules by molecular weight. This chromatography material is readily available. The preferred material is Ultrogel ACA 202 commercially available from LKB Corp., Gaithersburg, Md. As the fractions elute from the column they are typically assayed to localize phenylethanolamine N-methyltransferase activity by any one of several routine methods such as UV spectrometry, enzyme assays and the like.

Molecular size exclusion chromatography has two functions. First, the column has the ability to retain those molecules having a molecular weight of approximately 22,000 or less thereby effectively removing small molecules such as norepinephrine and epinephrine. Secondly, the column removes any salts and therefore facilitates subsequent anion-exchange chromatography.

The enzyme preparation is next applied to an anion-exchange chromatography column. Anion-exchange chromatography includes the use of a column material comprised of an alkylamine, for example a diethylaminoethyl or triethylaminoethyl moiety, covalently attached to any of a variety of matrices such as cellulose or any of a number of other polymers. A variety of these chromatographic materials are commercially available and the preferred material is sold by Pharmacia Chemicals as diethylaminoethyl-Sephacel. The column is previously equilibrated with a suitable buffer having a pH of approximately 8. The column is eluted with the same buffer until all non-adsorbed protein has been eluted. The enzyme activity is then eluted preferably with the same buffer containing sodium chloride, and the enzyme containing fractions are collected and concentrated by routine methods, such as by ultrafiltration.

Anion-exchange chromatography has two functions. First, cations such as norepinephrine and epinephrine will not bind to the column. Thus the column helps remove these interfering substances. Secondly, this column removes uncharacterized inhibitors of the enzyme reaction.

The concentrated enzyme preparation is next further purified with molecular size exclusion chromatography. The column is typically equilibrated with a buffer having a pH in the range of about 7.5 to 8.5 prior to the enzyme purification. The column is eluted with buffer and the fractions containing the enzyme are combined. Molecular size exclusion effectively removes smaller molecules capable of reducing the purity of the enzyme preparation.

The combined fractions containing the isolated enzyme are applied to a boronate-agarose chromatography column previously equilibrated with a potassium buffer at approximately pH 7.5 to 9.5, such as potassium HEPES. Boronate-agarose columns contain an agarose gel with bound borate. This material is capable of complexing cis-diols, such as catecholamines, and is thereby capable of further purifying the enzyme preparation by removing endogenous catecholamines. This material is commercially available in a variety of forms. The preferred material is PBA-60, a phenylboronate-agarose column commercially available from Amicon. As the column is eluted with the buffer, the nonabsorbed protein is typically collected as a single fraction. The collected enzyme solution is concentrated and suitable for use in a norepinephrine radioenzymatic assay. The boronate-agarose column has a very high capacity for catecholamines and as such this column is extremely valuable in the removal of residual norepinephrine and epinephrine.

The phenylethanolamine N-methyltransferase purification process as described above produces enzyme in substantially pure form and in high yield. The term "substantially pure form", as used herein, represents phenylethanolamine N-methyltransferase purified by the procedure taught herein to such a purity so as to be suitable for use in radioenzymatic assays. Several advantages have been observed for the present method of purification. For example, one purification scheme involving 30 bovine adrenal glands generated enough phenylethanolamine N-methyltransferase for approximately 25,000 standard assay tubes, and resulting in a total enzyme volume of approximately 60 ml. The entire purification scheme requires only a total of 3 to 4 working days in order to complete.

The present improved purification scheme for phenylethanolamine N-methyltransferase has produced a variety of unexpected results when using the purified enzyme in an appropriate norepinephrine radioenzymatic assay. The use of highly purified enzyme permits the use of a lesser quantity of [$^3$H]S-adenosylmethionine in the assay. This is important from a cost standpoint since radiolabeled reagents are expensive. Further, increased sensitivity of the assay makes it possible to process samples not previously suitable for analysis.

Finally the isolation of the radiolabeled catecholamine formed during the assay is now more efficient in light of the reduced number of impurities in the enzyme. All of these advantages yield a quick, efficient and inexpensive diagnostic procedure suitable for use by a minimally trained laboratory operator. This improved norepinephrine radioenzymatic assay is taught in application Ser. No. 627,319, filed even date herewith.

The phenylethanolamine N-methyltransferase purified by the process described above is preferably employed in a radioenzymatic assay capable of quantifying endogenous norepinephrine. The biochemical principle of the norepinephrine radioenzymatic assay is illustrated by the following reaction scheme:

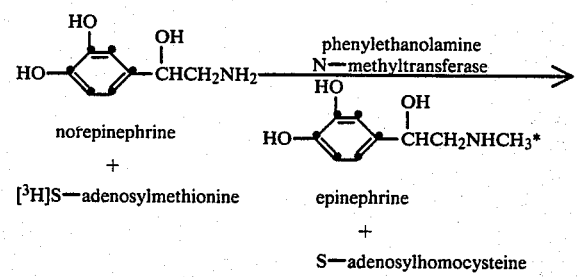

The exact amount of phenylethanolamine N-methyltransferase to be used in the norepinephrine radioenzymatic assay is determined by performing a titration of the enzyme and analyzing for the best sample to blank ratio. Generally from as little as approximately one to approximately five microliters of phenylethanolamine N-methyltransferase per assay tube may be employed and still provide optimum results.

The following example illustrates the purification of phenylethanolamine N-methyltransferase according to the method of the present invention. The example is not intended to be limiting to the scope of the present invention in any respect and should not be so construed.

ISOLATION OF PHENYLETHANOLAMINE N-METHYL TRANSFERASE

All steps in the following purification scheme were conducted in a temperature in the range of 0° C. to 4° C. The presence of the enzyme was followed employing a flow through absorbance monitor set at 280 nanometers.

Thirty fresh bovine adrenal glands were obtained and immediately immersed in ice cold saline. The glands were transported to the laboratory and the cortical tissue was removed by making an initial cut with a scalpal, localizing the cortex medulla tissue plane and teasing the respective tissues apart. The resulting 83 g of medullary tissue was minced with a razor blade, and homogenized with a Brinkmann Polytron following addition of 280 ml of a 0.25M sucrose solution. The homogenate was centrifuged at 40,000×g for 15 minutes and the supernatant was decanted and filtered through gauze. The supernatant was centrifuged at 220,000×g for 90 minutes. Ammonium sulfate (0.375 g per ml; 62% saturation) was slowly added to the supernatant. The mixture was stirred for 20 minutes and the preparation was centrifuged at 40,000×g for 10 minutes. The supernatant was discarded and the precipitate was resuspended with 50 ml of Buffer A. When used herein, the term "Buffer A" represents a solution comprising 50 mM of Trizma base (tris(hydroxymethyl- )aminomethane available from Sigma Chemical Company, St. Louis, Mo.) and 1 mM of EDTA at a pH of 8.

The enzyme preparation was adjusted to pH 5 by the slow addition of cold 2.0M acetic acid. This solution was stirred for 20 minutes and then centrifuged at 40,000×g for approximately 10 minutes. The supernatant was decanted to provide 55 ml of solution. This solution was transferred to three dialysis bags (employing Spectropore one membrane tubing; 6,000 to 8,000 molecular weight cutoff). The supernatant was dialyzed for 24 hours against 5 liters of a 10 mM solution of sodium acetate at pH 5. One buffer change was required during the procedure. The dialyzed preparation was centrifuged at 40,000×g for ten minutes and the precipitate was discarded. The supernatant was titrated to a pH of approximately 7.2 by the slow addition of 1M ammonium hydroxide. The solution was adjusted to a concentration of 1 mM by the addition of 100 mM dipotassium EDTA. The final enzyme volume was 80 ml.

The enzyme was next concentrated by precipitation by the addition of ammonium sulfate to the solution to provide a 70% saturated solution. The mixture was stirred for 20 minutes and the precipitate was collected by centrifugation at 40,000×g for 10 minutes. The precipitate was suspended with 10 ml of Buffer A. The enzyme was then applied to an Ultragel ACA-202 column (30 cm×2 cm) which had been previously equilibrated with Buffer A. The column was eluted at a flow rate of 0.75 ml per minute and, upon elution of the enzyme from the column, 7.5 ml fractions were collected. The fractions were assayed for phenylethanolamine N-methyltransferase and all of the fractions containing the enzyme were collected to provide 32 ml of an enzyme solution.

The enzyme containing fractions were next applied to a diethylaminoethyl-Sephacel column (5 cm×1.6 cm) which had been previously equilibrated with Buffer A. The column was eluted at a flow rate of 0.75 ml per minute with the same buffer until the 280 nm absorbance had returned completely to baseline. The phenylethanolamine N-methyltransferase was then eluted with Buffer A containing 0.5M sodium chloride. The enzyme was collected as a single fraction and concentrated to 10 ml in an Amicon ultrafiltration cell using a PM-10 Diaflo membrane.

The concentrated enzyme preparation prepared above was loaded on a Sephacryl-S200 column (80 cm×2 cm) which had been previously equilibrated with Buffer A. The column was eluted at a flow rate of 0.5 ml per minute and 6 ml fractions were collected therefrom. Column fractions containing the enzyme were then analyzed employing a standard enzyme assay.

The aliquot containing the enzyme was finally applied to a PBA-60 column (10 cm×1 cm) which had previously been equilibrated with a pH 8.5 buffer comprising 50 mM potassium HEPES and 1 mM EDTA. The column was then eluted with Buffer A. The nonabsorbed enzyme was collected as a single fraction and concentrated to afford approximately 30 ml of phenylethanolamine N-methyltransferase suitable for use in a norepinephrine radioenzymatic assay.

We claim:

1. A method for isolating phenylethanolamine N-methyltransferase in substantially pure form from enzyme containing mammalian tissues at a temperature in the range of about 0° C. to about 5° C. comprising the following steps:
   A. disrupting the mammalian tissue in the presence of an isotonic media and isolating the phenylethanolamine N-methyltransferase;
   B. fractionating the supernatant in (A) with ammonium sulfate at about 55% to about 85% saturation and collecting the precipitate;
   C. suspending the precipitate formed in (B) with a suitable buffer having a pH in the range of about 7.0 to 9.0;
   D. adjusting the pH of the suspension in (C) to about 4.5 to 5.5 with an appropriate weak acid;
   E. dialyzing the suspension in (D) against a sodium acetate buffer having a pH in the range of about 4.5 to 5.5;
   F. concentrating the enzyme preparation in (E) by ammonium sulfate fractionation at about 55% to about 85% saturation and desalting;
   G. purifying the enzyme preparation in (F) with anion-exchange chromatography;
   H. purifying the enzyme preparation in (G) with molecular size exclusion chromatography; and
   I. purifying the enzyme preparation in (H) with boronate-agarose chromatography.

2. A method of claim 1 wherein the mammalian tissue is adrenal gland.

3. A method of claim 2 wherein the adrenal gland is bovine adrenal gland.

4. A method of claim 1 wherein the isotonic media is sucrose.

5. A method of claim 1 wherein the appropriate weak acid is acetic acid.

* * * * *